United States Patent
Lin

(10) Patent No.: US 8,213,080 B2
(45) Date of Patent: Jul. 3, 2012

(54) INSPECTION APPARATUS FOR BIOLOGICAL SAMPLE

(75) Inventor: Kuang-Yuan Lin, Hsinchu (TW)

(73) Assignee: Shanghai Microtek Technology Co., Ltd., Shanghai (CN)

( * ) Notice: Subject to any disclaimer, the term of this patent is extended or adjusted under 35 U.S.C. 154(b) by 637 days.

(21) Appl. No.: 12/318,486

(22) Filed: Dec. 30, 2008

(65) Prior Publication Data

US 2010/0079749 A1 Apr. 1, 2010

(30) Foreign Application Priority Data

Sep. 26, 2008 (TW) .............................. 97217404 U

(51) Int. Cl.
*G01N 21/01* (2006.01)
*G02B 21/34* (2006.01)
(52) U.S. Cl. ........................................ 359/398; 356/246
(58) Field of Classification Search .......... 359/396–398; 422/527; 356/246
See application file for complete search history.

(56) References Cited

U.S. PATENT DOCUMENTS

| | | | | |
|---|---|---|---|---|
| 4,414,197 | A | * | 11/1983 | Dussault ................ 435/40.51 |
| 4,527,467 | A | * | 7/1985 | Siemensma .................. 99/279 |
| 5,019,351 | A | * | 5/1991 | Schulz ........................ 422/527 |
| 5,209,904 | A | * | 5/1993 | Forney et al. ................. 422/73 |
| 5,256,376 | A | * | 10/1993 | Callan et al. .................. 422/72 |
| 5,312,731 | A | * | 5/1994 | Engstrom ..................... 435/32 |
| 5,975,153 | A | * | 11/1999 | Hill et al. ..................... 141/31 |
| 7,663,101 | B2 | * | 2/2010 | Goodman ..................... 250/304 |
| 7,863,035 | B2 | * | 1/2011 | Clemens et al. ............. 435/287.1 |
| 7,919,308 | B2 | * | 4/2011 | Schleifer .................... 435/305.4 |
| 2006/0275893 | A1 | * | 12/2006 | Ishii et al. .................. 435/288.7 |
| 2009/0231576 | A1 | * | 9/2009 | Suppel-Adrian et al. ..... 356/246 |

* cited by examiner

*Primary Examiner* — Frank Font

(74) *Attorney, Agent, or Firm* — Rosenberg, Klein & Lee

(57) ABSTRACT

An inspection apparatus for a biological sample is herein disclosed, wherein a sample, entering a communicating space via a first opening, is sucked upward to a test area by capillarity and then sucked downward to a second opening by a siphonic action; then the sample becomes still as a result of the communicating tube principle. Hence, the present invention provides sufficient amount of biological sample for the test area and also simplifies the inspection process.

15 Claims, 4 Drawing Sheets

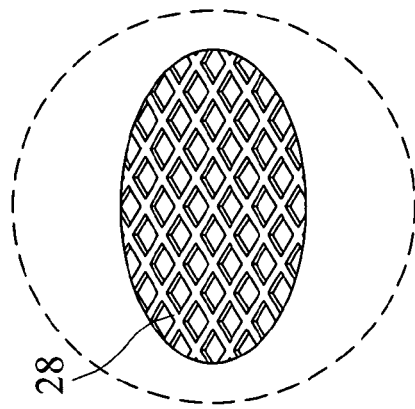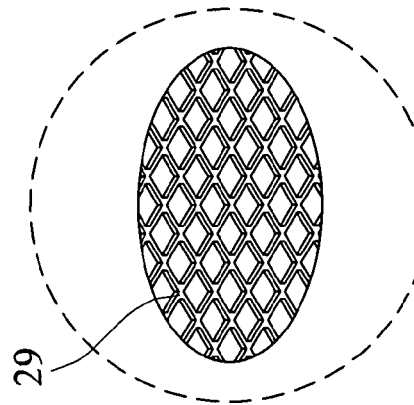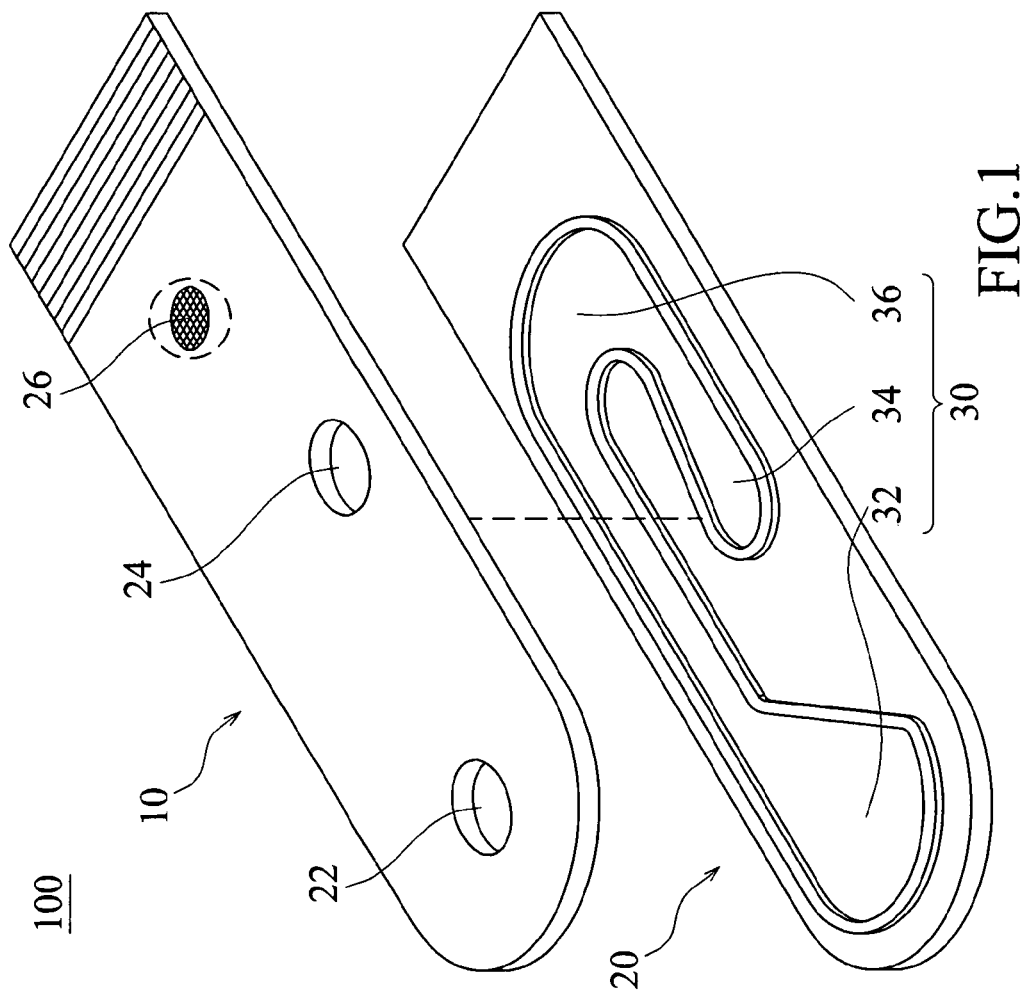

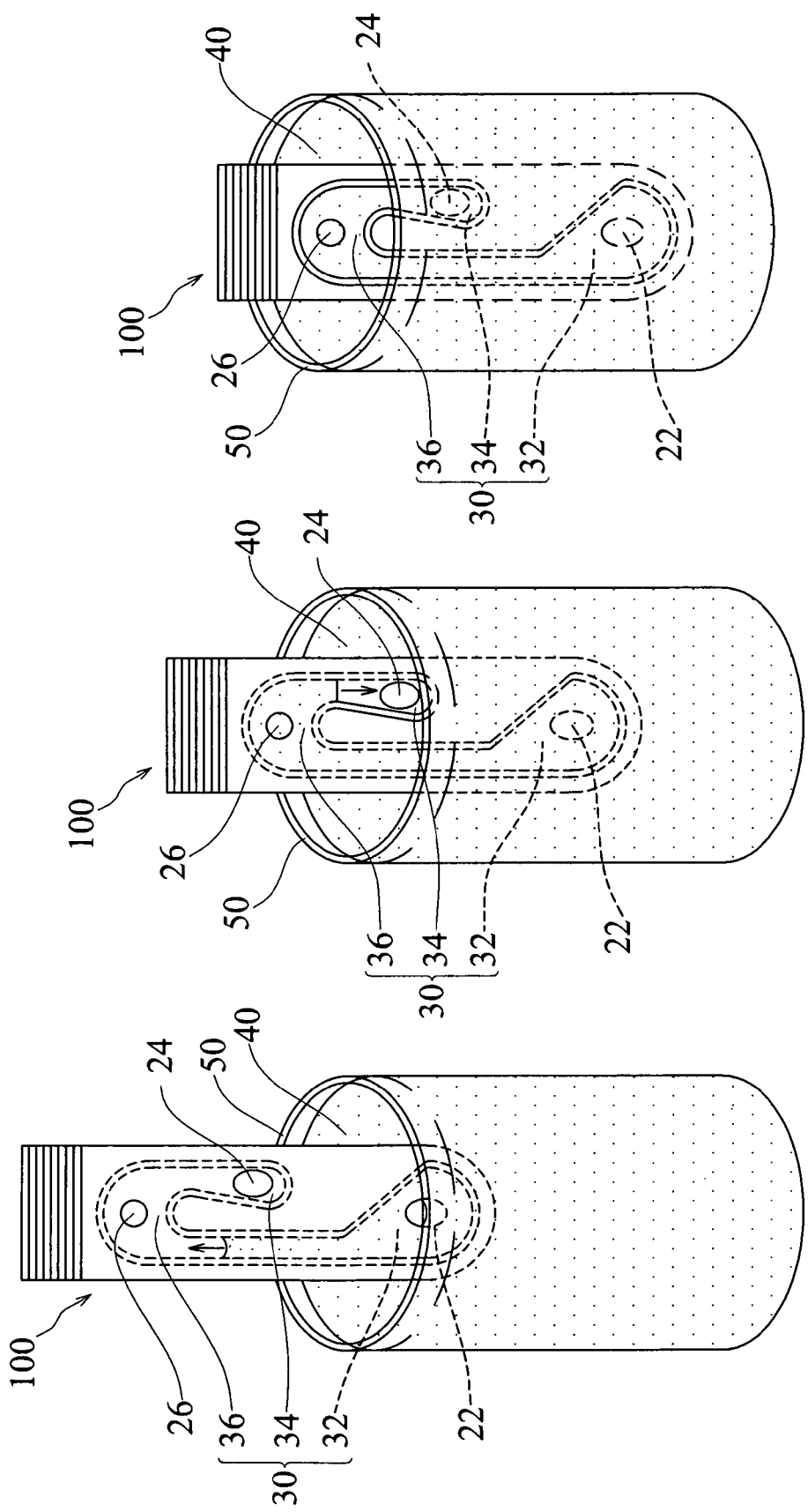

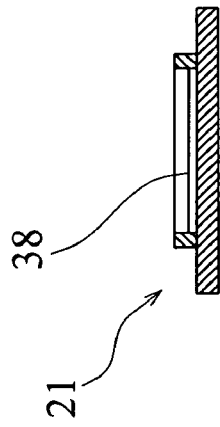
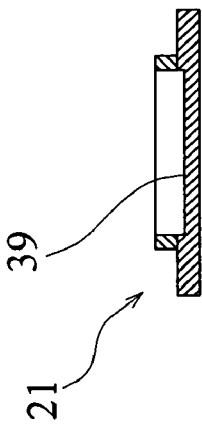
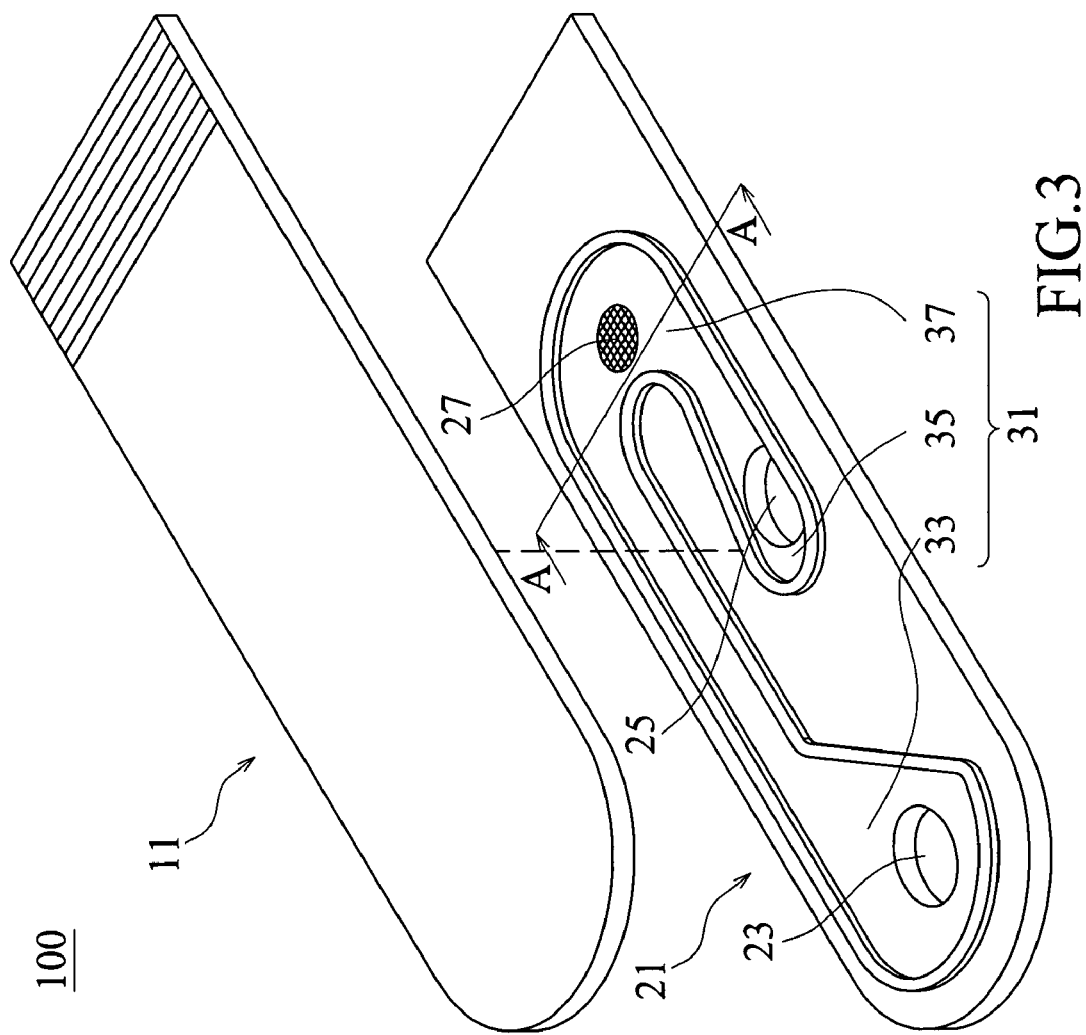

INSPECTION APPARATUS FOR BIOLOGICAL SAMPLE

BACKGROUND OF THE INVENTION

1. Field of the Invention

The present invention relates to a biological inspection technology, particularly to an inspection apparatus for a biological sample.

2. Description of the Related Art

Microscopic inspection of a biological sample usually uses an inspection apparatus with a microscope slide and a cover slip. A biological sample generally contains liquid and inspected objects, such as cells. Before biological inspection and microscopic counting, an appropriate amount of sample is dropped on a microscope slide, and then a cover slip is pressed onto the microscope slide to remove redundant liquid. Then, the tiny gap between the microscope slide and the cover slip contains a small amount of liquid and inspected objects for inspection and counting.

However, the inspection personnel's skin is likely to contact and pollute the biological sample in the gap between the microscope slide and cover slip in using the conventional inspection apparatus. Thus, the inspection devices are hard to attain accurate data. Further, the space between the microscope slide and the cover slip is hard to accurately control. Thus, the amount of a biological sample is also hard to determine. Therefore, there is still room to improve the accuracy and convenience of the conventional inspection apparatus.

A Taiwan patent No. 333564, issued on Jun. 1, 2008, disclosed a "Test Piece Structure for Body Fluid", which comprises an upper plate with a collecting hole, a middle plate with a ventilating hole, a biocarbon circuit layer, and a base plate with a stop member. The collecting hole of the upper plate collects a body fluid, and the siphon suction hole in the middle plate sucks in the body fluid. Then, the body fluid contacts the test terminals of the biocarbon circuit layer and triggers a biotest device to analyze the body fluid. The stop member of the base plate of the test piece props against the clip mechanism of the biotest device. After the test, the test piece is released from the clip mechanism. However, the inspection personnel's skin is also likely to contact collecting hole and pollute the sample, which results in incorrect test data.

The conventional inspection apparatus and the cited patent have their limitations. To attain correct test results, the conventional inspection apparatuses need improvements to prevent from collecting insufficient sample or personnel contacting to a sample.

SUMMARY OF THE INVENTION

One objective of the present invention is to provide an inspection apparatus for a biological sample, which can prevent from personnel contacting to the biological sample and provide an appropriate space for the inspected objects.

Another objective of the present invention is to provide an inspection apparatus for a biological sample, wherein a sample enters a communicating space via a first opening, is sucked toward a test area by capillarity, and then sucked downward to a second opening by a siphon action; then the sample becomes still as a result of a communicating tube principle, wherefore the present invention provides sufficient amount of biological sample for the test area and also simplifies the inspection process.

A further objective of the present invention is to provide an inspection apparatus for a biological sample, wherein an injection molding technology and optical molds are used to form a high-precision communicating space that can contain sufficient amount of biological sample and prevent from insufficiency of biological sample.

To achieve the abovementioned objectives, the present invention proposes an inspection apparatus for a biological sample, which includes a first glass plate and a second glass plate arranged over the first glass plate. A hook-like communicating space is formed in between the first glass plate and a second glass plate. The first glass plate has a first opening and a second opening respectively arranged corresponding to a root portion and a hook portion of the communicating space. A test area is formed on the first glass plate and arranged corresponding to a top portion of the hook-like communicating space. A biological sample, entering the communicating space via the first opening, is sucked toward the test area by capillarity and then sucked downward to the second opening by a siphon action; then the biological sample becomes still in the hook-like communicating space as a result of the communicating tube principle.

The present invention also proposes another inspection apparatus for a biological sample, which includes a cup body and a communicating tube structure. The communicating tube structure is formed on the cup wall of the cup body and has a first opening and a second opening respectively arranged corresponding to a cup base and a cup rim of the cup body. The communicating tube structure extends from the cup base to a top portion and then extends toward and runs through the cup base and then extends again to the second opening on the cup rim. The top portion is higher than the cup rim of the cup body and has a test area. A biological sample, poured into the cup body and entering the communicating tube structure via the first opening, is sucked toward the top portion by capillarity and then sucked downward through the cup base and then sucked again to reach the second opening by a siphonic action. When the biological sample is going to overflow the second opening, it stops flowing and becomes still as a result of the communicating tube principle.

BRIEF DESCRIPTION OF THE DRAWINGS

FIG. 1 is a perspective exploded view schematically showing a disposable inspection apparatus according to one preferred embodiment of the present invention;

FIG. 1-1 is a partially-enlarged view schematically showing a test area according to one preferred embodiment of the present invention;

FIG. 1-2 is a partially-enlarged view schematically showing another test area according to one preferred embodiment of the present invention;

FIGS. 2-1 is a perspective view schematically showing that a biological sample is sucked from a root portion to a top portion by capillarity according to one preferred embodiment of the present invention;

FIGS. 2-2 is a perspective view schematically showing that a biological sample is sucked downward from a top portion to a hook portion by a siphonic action according to one preferred embodiment of the present invention;

FIG. 2-3 is a perspective view schematically showing that a biological sample becomes still as a result of a communicating tube principle according to one preferred embodiment of the present invention;

FIG. 3 is a perspective exploded view schematically showing a disposable inspection apparatus according to another preferred embodiment of the present invention;

FIG. 3-1 is a sectional view along Line A-A in FIG. 3 schematically showing a bottom-convexed basin;

FIG. 3-2 is another sectional view along Line A-A in FIG. 3 schematically showing a bottom-recessed basin;

FIG. 4-1 is a top view schematically showing a cup type inspection apparatus according to a further preferred embodiment of the present invention; and FIG. 4-2 is a sectional view schematically showing a cup type inspection apparatus according to a further preferred embodiment of the present invention.

DETAILED DESCRIPTION OF THE INVENTION

Below, the embodiments will be described in detail in cooperation with the attached drawings to demonstrate the technical contents and characteristics of the present invention.

Figures 1, 4:
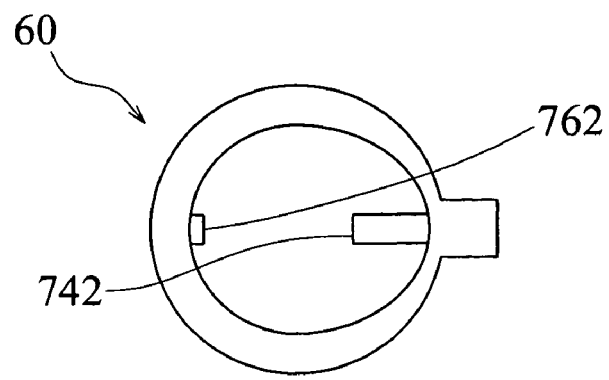
Figures 2, 4:
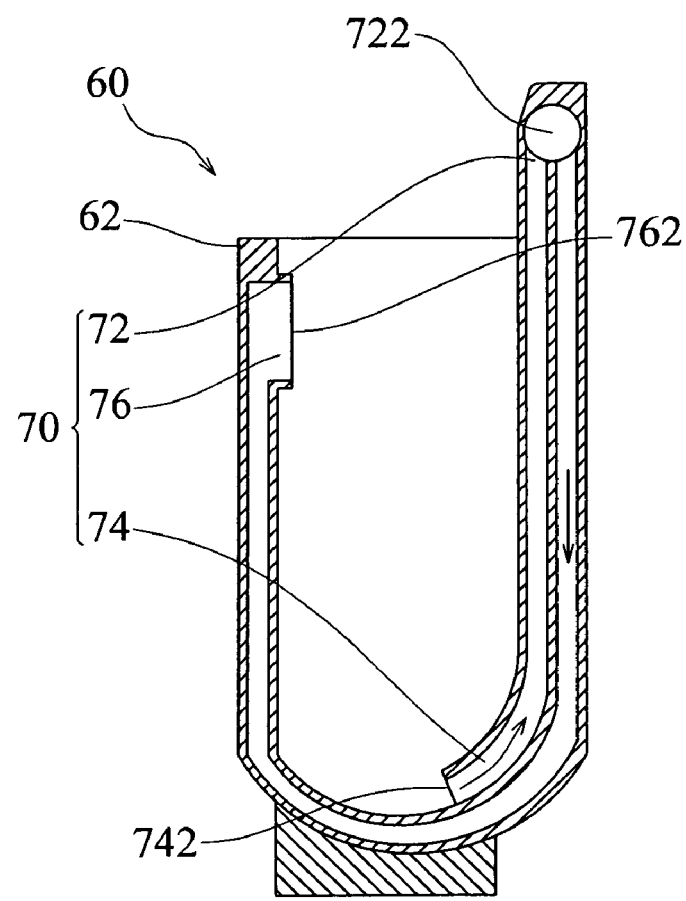

Refer to FIG. 1, FIG. 1-1, FIG. 1-2, FIG. 2-1, FIG. 2-2, and FIG. 2-3 for an inspection apparatus for a biological sample according to a preferred embodiment of the present invention.

Referring to FIG. 1, a perspective exploded view of a disposable inspection apparatus 100 according to a preferred embodiment of the present invention is provided. The disposable inspection apparatus 100 comprises a first glass plate 10 and a second glass plate 20, wherein the first glass plate 10 and the second glass plate 20 can be assembled together. A hook-like communicating space 30 is formed in between the first glass plate 10 and the second plate 20 with an injection molding technology and optical molds. The first glass plate 10 has a first opening 22 and a second opening 24 respectively arranged corresponding to a root portion 32 and a hook portion 34 of the hook-like communicating space 30. The first glass plate 10 has a test area 26 having a height of about 3 nm-100 µm and arranged in a top portion 36 of the hook-like communicating space 30. Referring to FIG. 1-1 and FIGS. 1-2, the test area 26 has grid lines, and the grid lines may be inscribed lines 29 or convexed lines 28. The root portion 32, the top portion 36 and the hook portion 34 interconnect each other.

Refer to FIGS. 2-1. The inspection apparatus 100 is partially immersed in a biological sample 40 contained in a container 50. The biological sample 40 passes through the first opening 22 and reaches the root portion 32. The biological sample 40 can overcome the gravity and ascend to the top portion 36 via the difference of the adhesive force and the cohesive force of the biological sample 40 in the root portion 32. In other words, the biological sample 40 is sucked up from the root portion 32 to the top portion 36 by capillarity.

Refer to FIGS. 2-2. The first opening 22 in the root portion 32 sustains the atmospheric pressure and the liquid pressure of the biological sample 40. The second opening 24 in the hook portion 34 sustains only the atmospheric pressure. The biological sample 40 thus flows from a place of a higher pressure to another place of a lower pressure. Therefore, when reaching the top portion 36, the biological sample 40 will further flow to the second opening 24 because of the siphonic action.

Refer to FIG. 2-3. When the hook portion 34 of the hook-like communicating space 30 is immersed in the biological sample 40, the second opening 24 in the hook portion 34 sustains the same pressure as the first opening 22 in the root portion 32 does. Thus, the biological sample 40 shifts from a mobile state to an immobile state as a result of the communicating tube principle. Thus, the biological sample 40 on the test area 26 can be inspected microscopically.

After formed with an injection molding technology and optical molds, the first glass plate 10 and the second glass plate 20 needn't be processed with any additional fabrication step because the optical molds have a higher precision. In the present invention, the one-piece design of the first glass plate 10 and the second glass plate 20 not only simplifies the fabrication process but also reduce the cost.

In the abovementioned embodiment, the first opening 22, the second opening 24 and the test area 26 are formed on the first glass plate 10. Refer to FIG. 3. In another embodiment, a first opening 23, a second opening 25 and a test area 27 are formed on a second glass plate 21 and respectively arranged corresponding to a root portion 33, a hook portion 35 and a top portion 37 of a hook-like communicating space 31; a first glass plate 11 is free of any opening but can be assembled together with the second glass plate 21.

The hook-like communicating space 31 is formed in between the first glass plate 11 and the second glass plate 21 with an injection molding technology and optical molds and has a width of about 1 µm-3 mm and a height of about 0.1 µm-100 µm. Refer to FIG. 3-1 and FIG. 3-2. The second glass plate 21 may further have a bottom-recessed basin 39 or a bottom-convexed basin 38 corresponding to the hook-like communicating space 31, whereby the hook-like communicating space 31 can contain more biological sample or less biological sample.

Refer to FIG. 4-1 and FIG. 4-2 for a further preferred embodiment.

Refer to FIGS. 4-2 a sectional view of a cup type inspection apparatus according to a further preferred embodiment of the present invention. The cup type inspection apparatus comprises a cup body 60. A communicating tube structure 70 is formed on the cup wall 62 with an injection molding technology and optical molds. The communicating tube structure 70 has an inner diameter of about 1 µm-3 mm. The communicating tube structure 70 includes a first opening 742 and a second opening 762 respectively arranged on a cup base 74 and a cup rim 76. The communicating tube structure 70 extends from the first opening 742 to a top portion 72 and then extends downward and runs through the cup base 74 and then extends again to the second opening 762 on the cup rim 76.

The top portion 72 is higher than the cup rim 76 of the cup body 60. A test area 722 is formed on the top portion 72 and has a diameter of about 3 nm-100 µm. Refer to FIGS. 1-1 and FIGS. 1-2 also. The test area 722 has grid lines, and the grid lines may be inscribed lines 29 or convexed lines 28. The cup base 74, the top portion 72 and the cup rim 76 interconnect each other.

After poured into the cup body 60, the biological sample enters the communicating tube structure 70 from the first opening 742. The difference of the adhesive force and the cohesive force of the biological sample in the communicating tube structure 70 makes the biological sample able to overcome the gravity and ascend. Thus, the biological sample is sucked up from the cup base 74 through the first opening 742 to the top portion 72 by capillarity.

The first opening 742 on the cup base 74 sustains the atmospheric pressure and the liquid pressure of the biological sample, but the second opening 762 on the cup rim 76 sustains only the atmospheric pressure. The greater pressure forces the biological sample to flow toward the place of a smaller pressure. Therefore, after passing through the test area 722, the biological sample is sucked toward the second opening 762 by a siphonic action.

When the biological sample rises to the second opening 762 on the cup rim 76, the first opening 642 on the cup base 74 sustains the same pressure as the second opening 762 on the cup rim 76 does. Thus, the biological sample shifts from a mobile state to an immobile state as a result of the communicating tube principle. Thus, the biological sample on the test area 722 can be inspected microscopically.

In conclusion, the present invention proposes an inspection apparatus for a biological sample, which can prevent from personnel contacting to the biological sample and provide a space to contain an accurate amount of biological sample. After entering the hook-like communicating space from the first opening, the biological sample is sucked toward the test area by capillarity. After passing through test area, the biological sample is sucked downward to the second opening by a siphonic action. Thus, the biological sample becomes still as a result of the communicating tube principle. Then, the test area has sufficient biological sample for microscopic inspection, and the inspection process is simplified thereby. Besides, the present invention uses an injection molding technology and optical molds to form a high precision hook-like communicating space to contain the biological sample and avoid insufficiency of biological sample.

The embodiments described above are to demonstrate the technical thoughts and characteristics of the present invention to enable the persons skilled in the art to understand, make, and use the present invention. However, it is not intended to limit the scope of the present invention. Any equivalent modification or variation according to the spirit of the present invention is to be also included within the scope of the present invention.

What is claimed is:

1. An inspection apparatus for a biological sample, comprising
    a first glass plate; and
    a second glass plate arranged over said first glass plate, wherein
        a hook-like communicating space is formed in between said first glass plate and said second glass plate;
        said first glass plate has a first opening and a second opening respectively arranged corresponding to a root portion and a hook portion of said hook-like communicating space; and
    a test area is formed on said first glass plate and arranged in a top portion of said hook-like communicating space, whereby said biological sample entering said hook-like communicating space from said first opening is sucked toward said top portion by capillarity and sucked toward said second opening by a siphonic action; and said biological sample becomes still in said hook-like communicating space as a result of a communicating tube principle.

2. The inspection apparatus for a biological sample according to claim 1, wherein said hook-like communicating space has a width of about 1 μm-3 mm.

3. The inspection apparatus for a biological sample according to claim 1, wherein said hook-like communicating space has a height of about 0.1 μm-100 μm.

4. The inspection apparatus for a biological sample according to claim 1, wherein said test area has a diameter of about 3 nm-100 μm.

5. The inspection apparatus for a biological sample according to claim 1, wherein said second glass plate has a bottom-recessed basin corresponding to said hook-like communicating space.

6. The inspection apparatus for a biological sample according to claim 1, wherein said second glass plate has a bottom-convexed basin corresponding to said hook-like communicating space.

7. The inspection apparatus for a biological sample according to claim 1, wherein each of said first glass plate and said second glass plate is a one-piece component.

8. The inspection apparatus for a biological sample according to claim 1, wherein said test area has grid lines formed on said first glass plate.

9. The inspection apparatus for a biological sample according to claim 8, wherein said grid lines are inscribed lines or convexed lines.

10. The inspection apparatus for a biological sample according to claim 1, wherein said first opening, said second opening and said test area are formed on said second glass plate and respectively arranged corresponding to said root portion, said hook portion and said top portion of said hook-like communicating space.

11. An inspection apparatus for a biological sample, comprising
    a cup body; and
    a communicating tube structure, wherein
        said communicating tube structure includes a first opening and a second opening respectively arranged on a cup base and a cup rim of said cup body;
        said communicating tube structure extends upward from said first opening to a top portion and extends downward and through said cup base and extends upward again to said second opening on said cup rim;
        said top portion is higher than said cup rim of said cup body; and
    a test area is formed on said top portion, whereby the biological sample poured into said cup body enters said communicating tube structure from said first opening and is sucked toward said top portion by capillarity, sucked toward said cup base and sucked toward said second opening by a siphonic action; and said biological sample becomes still in said communicating tube structure as a result of a communicating tube principle.

12. The inspection apparatus for a biological sample according to claim 11, wherein said communicating tube structure has an inner diameter of about 1 μm-3 mm.

13. The inspection apparatus for a biological sample according to claim 11, wherein said test area has a diameter of about 3 nm-100 μm.

14. The inspection apparatus for a biological sample according to claim 11, wherein said test area has grid lines.

15. The inspection apparatus for a biological sample according to claim 14, wherein said grid lines are inscribed lines or convexed lines.

* * * * *